United States Patent

Tarumi et al.

[11] Patent Number: 6,080,452
[45] Date of Patent: *Jun. 27, 2000

[54] ELECTRO-OPTICAL LIQUID-CRYSTAL DISPLAY

[75] Inventors: Kazuaki Tarumi, Seeheim; Andreas Beyer, Hanau; Eike Poetsch, Mühltal, all of Germany

[73] Assignee: Merck Patent Gesellschaft mit Beschrankter Haftung, Germany

[*] Notice: This patent is subject to a terminal disclaimer.

[21] Appl. No.: 09/318,576

[22] Filed: May 27, 1999

Related U.S. Application Data

[62] Division of application No. 08/986,334, Dec. 5, 1997, Pat. No. 5,919,396.

[30] Foreign Application Priority Data

Dec. 5, 1996 [DE] Germany .............. 196 50 634

[51] Int. Cl.[7] .......... C09K 19/52; C09K 19/30; G02F 1/1337
[52] U.S. Cl. .............. 428/1.1; 252/299.01; 252/299.61; 252/299.62; 252/299.63; 252/299.66; 252/299.67; 349/132
[58] Field of Search .......... 252/299.01, 299.63, 252/299.64, 299.65, 299.66, 299.62, 299.67; 349/132, 191; 428/1.1

[56] References Cited

U.S. PATENT DOCUMENTS

| | | | |
|---|---|---|---|
| 5,403,512 | 4/1995 | Bartmann et al. | 252/299.01 |
| 5,576,867 | 11/1996 | Baur et al. | 349/39 |
| 5,598,285 | 1/1997 | Kondo et al. | 349/142 |
| 5,723,682 | 3/1998 | Poetsch et al. | 568/655 |
| 5,919,396 | 7/1999 | Tarumi et al. | 252/299.01 |

*Primary Examiner*—Shean C. Wu
*Attorney, Agent, or Firm*—Millen, White, Zelano & Branigan, P.C.

[57] ABSTRACT

The invention relates to an electro-optical liquid-crystal display having a realignment layer for realigning the liquid crystals whose field has a significant component parallel to the liquid-crystal layer and which contains a liquid-crystalline medium of positive dielectric anisotropy, where the medium comprises at least one mesogenic compound of the formula II

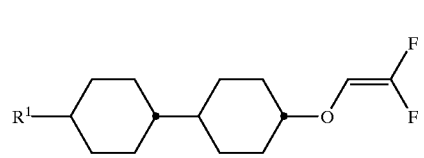

in which $R^1$ is H, an alkyl or alkenyl radical having 1 to 15 carbon atoms which is unsubstituted or monosubstituted or polysubstituted by halogen and in which one or more $CH_2$ groups may each, independently of one another, be replaced by —O—, —S—, —CO—, —COO—, —OCO— or —OCO—O— in such a way that O atoms are not linked directly to one another.

18 Claims, No Drawings

ELECTRO-OPTICAL LIQUID-CRYSTAL DISPLAY

This is a divisional, of application Ser. No. 08/986,334 filed Dec. 5, 1997, now U.S. Pat. No. 5,919,396.

The invention relates to an electro-optical liquid-crystal display having a realignment layer for realigning the liquid crystals whose field has a significant component parallel to the liquid-crystal layer and which contains a liquid-crystalline medium of positive dielectric anisotropy, where the medium comprises at least one mesogenic compound of the formula II:

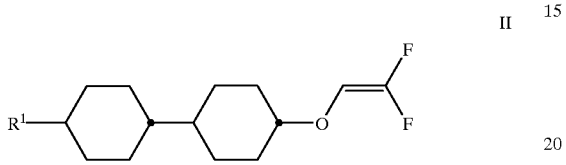

II in which $R^1$ is an alkyl or alkenyl radical having 1 to 15 carbon atoms which is unsubstituted or monosubstituted to perhalo-substituted by halogen and in which one or more $CH_2$ groups may each, independently of one another, be replaced by —O—, —S—, —CO—, —COO—, —OCO— or —OCO—O— in such a way that O atoms are not linked directly to one another.

In conventional liquid-crystal displays (TN, STN, OMI or AMD-TN), the electric fields for realignment are generated essentially perpendicular to the liquid-crystal layer.

International patent application WO 91/10936 discloses a liquid-crystal display in which the electric signals are generated in such a way that the electric fields have a significant component parallel to the liquid-crystal layer (IPS, in-plane switching). The principles of operating such a display are described, for example, by R. A. Soref in Journal of Applied Physics, vol. 45, No. 12, pp. 5466–5468 (1974).

EP 0 588 568 discloses various ways of addressing a display of this type.

These IPS displays can be operated with liquid-crystalline materials either of positive or of negative dielectric anisotropy ($\Delta\epsilon \ne 0$). However, using the materials known hitherto, relatively high threshold voltages and long response times are achieved in IPS displays. An object was therefore to indicate liquid-crystalline materials which are suitable for achieving relatively low threshold voltages and short response times in IPS displays.

Surprisingly, this object has been achieved by the use of liquid-crystalline materials comprising at least one compound of the formula II.

Upon further study of the specification and appended claims, further objects and advantages of this invention will become apparent to those skilled in the art.

The invention therefore relates to an electrooptical liquid-crystal display having a realignment layer for realigning the liquid crystals whose field has a significant component parallel to the liquid-crystal layer and which contains a liquid-crystalline medium of positive dielectric anisotropy, where the medium comprises at least one mesogenic compound of the formula II

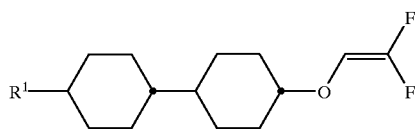

II in which

R is H, an alkyl or alkenyl radical having 1 to 15 carbon atoms which is unsubstituted or monosubstituted to perhalo-substituted by halogen and in which one or more $CH_2$ groups may each, independently of one another, be replaced by —O—, —S—, —CO—, —COO—, —OCO— or —OCO—O— in such a way that O atoms are not linked directly to one another.

Preferred embodiments are IPS displays in which a) the medium additionally comprises at least one compound of the formula I:

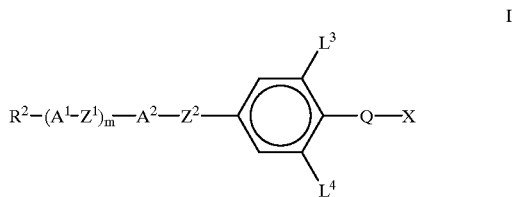

I in which $R^2$ is H, an alkyl or alkenyl radical having 1 to 15 carbon atoms which is unsubstituted, monosubstituted by CN or $CF_3$, or monosubstituted to perhalo-substituted by halogen, where one or more $CH_2$ groups in these radicals may also, in each case independently of one another, be replaced by —O—, —S—,

—CO—, —CO—O—, —O—CO— or —O—CO—O— in such a way that O atoms are not linked directly to one another, Q is a radical of the formula

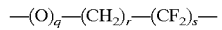

in which q is 0 or 1, r is 0 or an integer from 1 to 6, and s is 0 or an integer from 1 to 6, X is F or Cl, and in the case where s=1–6, is alternatively H, and p is 0, 1 or 2, $A^1$ and $A^2$ are each, independently of one another, (a) a trans-1,4-cyclohexylene radical or 1,4-cyclohexenylene radical, in which, in addition to one or more non-adjacent $CH_2$ groups may be replaced by —O— and/or —S—, (b) a 1,4-phenylene radical, in which, in addition, one or two CH groups may be replaced by N, (c) a radical selected from the group consisting of 1,4-dicyclo[2.2.2]-octylene, piperidine-1,4-diyl, naphthalene-2,6-diyl, decahydronaphthalene-2,6-diyl and 1,2,3,4-tetrahydronaphthalene-2,6-diyl, where the radicals (a) and (b) may be substituted by one or two fluorine atoms, $L^3$ and $L^4$ are H or F, $Z^1$ and $Z^2$ are each independently of one another, —CO—O—, —O—CO—, —CH$_2$O—, —OCH$_2$—, —CH$_2$CH$_2$—, —CH=CH—, —C≡C—, or a single bond, or one of the radicals $Z^1$ and $Z^2$ is —(CH$_2$)$_4$— or —CH=CH—CH$_2$CH$_2$—, and m is 0, 1 or 2;

b) the medium comprises at least one compound of the formula IIa:

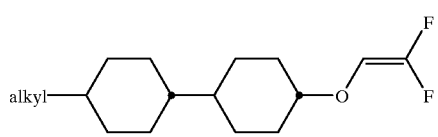

IIa in which alkyl is an alkyl group having 1 to 8 carbon atoms;

c) the medium additionally comprises at least one compound of the formula III

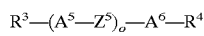

III in which $R^3$ and $R^4$ are each, independently of one another, as defined for $R^2$ in the formula I, $A^5$ and $A^6$ are each, independently of one another, as defined for $A^1$ and $A^2$, $Z^5$ is in each case, independently of the others, as defined for $Z^1$ and $Z^2$ in the formula I, and o is 1, 2 or 3;

d) the medium additionally comprises at least one compound of the formula IV

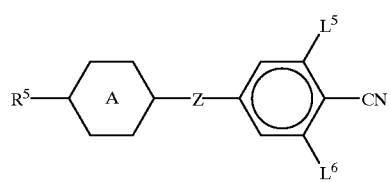

IV in which $R^5$ is as defined for $R^2$ in formula I:

Z is a single bond or —COO—, and $L^5$ and $L^6$ are each F or H.

Preference is furthermore given to an IPS display in which the pixels are addressed by means of an active matrix.

The invention furthermore relates to a liquid-crystalline medium of positive dielectric anisotropy which comprises at least one compound of the formula I and at least one compound of the formula II, in particular which comprises:

| from 50 to 95% by weight, | preferably from 60 to 80% by weight, of at least one compound of the formula I, |
|---|---|
| from 2 to 25% by weight, | preferably from 3 to 15% by weight, of at least one compound of the formula II, |
| from 0 to 30% by weight, | preferably from 5 to 25% by weight, of at least one compound of the formula III, and |
| from 5 to 35% by weight, | preferably from 8 to 25% by weight of a compound of the formula IV. |

The medium preferably comprises:

at least one compound selected from the formulae Ia, Ib and Ic:

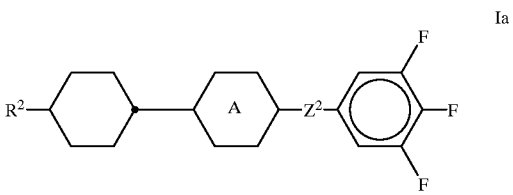

Ia

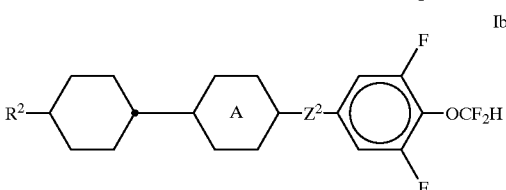

Ib

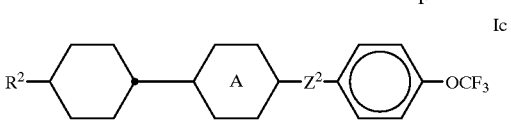

Ic if desired, at least one compound selected from the formulae IIIa, IIIb and IIIc:

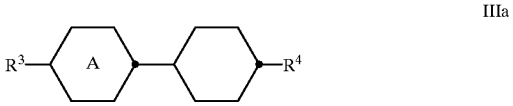

IIIa

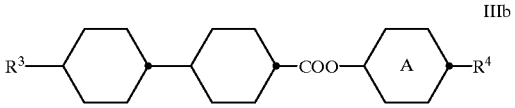

IIIb

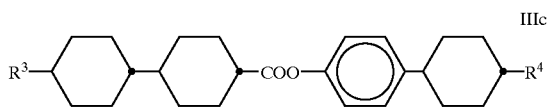

IIIc and at least one compound selected from the formulae IVa to IVd:

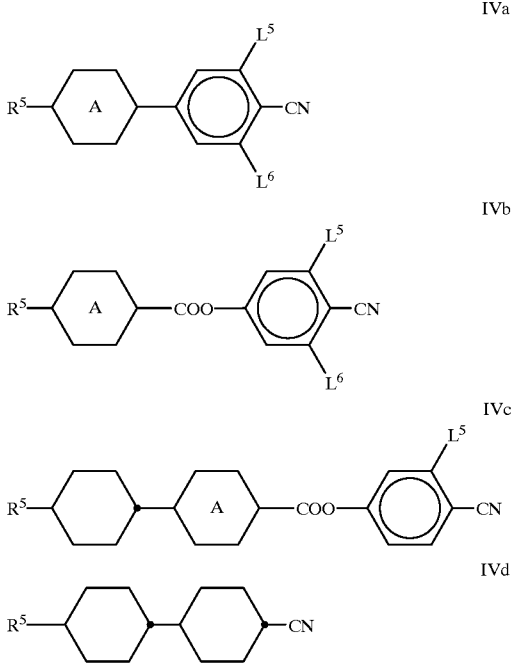

in which

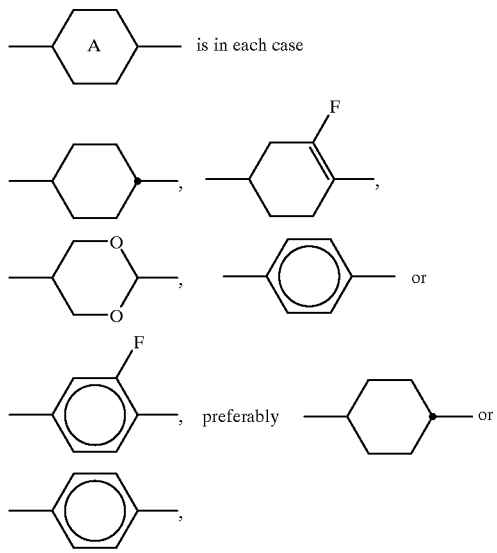

and
Z² is —COO—, —CH₂CH₂— or a single bond,
and $R^2, R^3, R^4, R^5, L^5$ and $L^6$ are each as defined above.

The novel liquid-crystalline media generally have a birefringence (Δn) of <0.12, preferably from 0.05 to 0.1, in particular from 0.065 to 0.08.

The flow viscosity (at 20° C.) of the novel materials is generally less than 30 mm² s⁻¹, in particular from 15 to 25 mm² s⁻¹. The rotational viscosity of the novel media is generally less than 200 mPa·s, preferably less than 150 mPa·s, in particular from 70 to 100 mPa·s.

It has been found that even a relatively small proportion of compounds of 2-fluorovinyloxycyclohexyl derivatives in a mixture with conventional liquid-crystal materials, but in particular with one or more compounds of the formula I, III and/or IV, results in a significant lowering of the threshold voltage and in fast response times, with at the same time broad nematic phases having low smectic-nematic transition temperatures being observed. A further advantage of the novel liquid-crystal materials is their comparatively low birefringence. The compounds of the formulae I to IV are colorless, stable and readily miscible with one another and other liquid-crystal materials.

The term "alkyl" covers straight-chain and branched alkyl groups having 1–7 carbon atoms, in particular the straight-chain groups methyl, ethyl, propyl, butyl, pentyl, hexyl and heptyl. Groups having 2–5 carbon atoms are generally preferred.

The term "alkenyl" covers straight-chain and branched alkenyl groups having 2–7 carbon atoms, in 30 particular the straight-chain groups. Particular alkenyl groups are $C_2$–$C_7$-1E-alkenyl, $C_4$–$C_7$-3E-alkenyl, $C_5$–$C_7$-4-alkenyl, $C_6$–$C_7$-5-alkenyl and $C_7$-6-alkenyl, in particular $C_2$–$C_7$-1E-alkenyl, $C_4$–$C_7$-3E-alkenyl and $C_5$–$C_7$-4-alkenyl. Examples of preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having 2 to 5 carbon atoms are generally preferred for alkenyl groups.

The term "fluoroalkyl" preferably covers the straight-chain groups having a terminal fluorine atom, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" preferably covers straight-chain radicals of the formula $C_nH_{2n+1}$—O—$(CH_2)_m$, in which n and m are each, independently of one another, from 1 to 6. Preferably, n=1 and m is from 1 to 6.

Through a suitable choice of the meanings of $R^1$ and $R^5$, the response times, the threshold voltage, the steepness of the transmission characteristic lines, etc., can be modified as desired. For example, 1E-alkenyl radicals, 3E-alkenyl radicals, 2E-alkenyloxy radicals and the like generally result in shorter response times, improved nematic tendencies and a higher ratio between the elastic constants $k_{33}$ (bend) and $k_{11}$ (splay) compared with alkyl and alkoxy radicals. 4-Alkenyl radicals, 3-alkenyl radicals and the like generally result in lower threshold voltages and smaller values of $k_{33}/k_{11}$ compared with alkyl and alkoxy radicals.

A —CH₂CH₂— group in $Z^1$ or $Z^2$ generally results in higher values of $k_{33}/k_{11}$ compared with a single covalent bond. Higher values of $k_{33}/k_{11}$ facilitate, for example, flatter transmission characteristic lines in TN cells having a 90° twist (for achieving gray shades) and steeper transmission characteristic lines in STN, SBE and OMI cells (greater multiplexibility), and vice versa.

The optimum mixing ratio between the compounds of the formulae I and II+III+IV depends substantially on the desired properties, on the choice of the components of the formulae I, II, III and/or IV and on the choice of any other components present. Suitable mixing ratios within the abovementioned range can easily be determined from case to case.

The total amount of compounds of the formulae I to IV in the novel mixtures is not crucial. The mixtures may therefore contain one or more further components in order to optimize various properties. However, the observed effect on the response times and the threshold voltage is generally higher the greater the total concentration of compounds of the formulae I and II.

The novel liquid-crystalline media preferably comprise 2 to 40, in particular 4 to 30, components as further constituents besides one or more compounds of the formulae I, II, III and IV. These media very particularly preferably comprise 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-bis-cyclohexybenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenyl-cyclo-hexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of novel media can be characterized by the formulae 1, 2, 3, 4 and 5:

$$R'-L-E-R''  \quad 1$$
$$R'-L-COO-E-R'' \quad 2$$
$$R'-L-OOC-E-R'' \quad 3$$
$$R'-L-CH_2CH_2-E-R'' \quad 4$$
$$R'-L-C\equiv C-E-R'' \quad 5$$

In the formulae 1, 2, 3, 4 and 5, L and E, which may be identical or different, are in each case, independently of one another, a bivalent radical from the group formed by —Phe—, —Cyc—, —Phe—Phe—, —Phe—Cyc—, —Cyc—Cyc—, —Pyr—, —Dio—, —G—Phe— and —G—Cyc— and their mirror images, where Phe is unsubstituted or fluorinesubstituted 1,4-phenylene, Cyc is trans-1,4-cyclo-hexylene or 1,4-cyclohexylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe—Cyc. The novel media preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of —Phe—Phe—, —Phe—Cyc—, —Cyc—Cyc—, —G—Phe— and —G—Cyc—, and optionally one or more components selected from the compounds of the formulae 1, 2, 3, 4 and 5 in which the radicals L and E are selected from the group consisting of —Phe—Cyc—, —Cyc—Cyc—, —G—Phe— and —G—Cyc—.

In a smaller sub-group of the compounds of the formulae 1, 2, 3, 4 and 5, R' and R" are in each case, independently of one another, alkyl, alkenyl, alkoxy, alkoxyalkyl, alkenyloxy or alkanoyloxy having up to 8 carbon atoms. This smaller sub-group is called group A below, and the compounds are labelled with the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5 which is known as group B, R" is —F, —Cl, —NCS or —(O)$_i$CH$_{3-(k+l)}$F$_k$Cl$_l$, where i is 0 or 1, and k+l is 1, 2 or 3; the compounds in which R" has this meaning are labelled with the sub-formulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is —CN; this sub-group is known as group C below, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides compounds of the formula I according to the invention, the novel media preferably contain one or more compounds selected from group A and/or group B and/or group C. The proportions by weight of the compounds from these groups in the novel media are preferably Group A: 0 to 90%, preferably 20 to 90%, in particular 30 to 90%

Group B: 0 to 80%, preferably 10 to 80%, in particular 10 to 65%

Group C: 0 to 80%, preferably 5 to 80%, in particular 5 to 50%, the sum of the proportions by weight of the group A and/or B and/or C compounds present in the particular novel media preferably being 5% to 90% and in particular 10% to 90%.

The novel media preferably comprise 1 to 40A, particularly preferably 5 to 30%, of compounds according to the invention. Further preferred media are those which contain more than 40%, in particular 45 to 90%, of compounds according to the invention. The media preferably contain three, four or five compounds according to the invention.

The structure of the IPS display according to the invention corresponds to the usual construction for such displays, as described, for example, in WO 91/10936 or EP 0 588 568. The term conventional construction is broadly drawn here and also covers all derivatives and modifications of the IPS display, in particular, for example, including matrix display elements based on poly-Si TFT or MIM.

However, an essential difference between the displays according to the invention and those conventional hitherto is in the choice of the liquid-crystal parameters of the liquid-crystal layer.

The liquid-crystal mixtures which can be used in accordance with the invention are prepared in a manner conventional per se. In general, the desired amount of the components used in lesser amount is dissolved in the components making up the principal constituent, expediently at elevated temperature. It is also possible to mix solutions of the components in an organic solvent, for example in acetone, chloroform or methanol, and, after mixing, to remove the solvent again, for example by distillation.

The compounds of the formulae I to IV are prepared by methods known per se, as described in the literature (for example in the standard works, such as Houben-Weyl, Methoden der Organischen Chemie, Georg-Thieme-Verlag, Stuttgart), to be precise under reaction conditions which are known and are suitable for said reactions.

Use may also be made here of variants which are known per se, but are not described here in greater detail.

If desired, the starting materials can also be formed in situ by not isolating them from the reaction mixture, but instead immediately converting them further into the compounds of the formulae I–IV.

The compounds of the formula II can be prepared in a simple manner, for example as shown in the reaction scheme below.

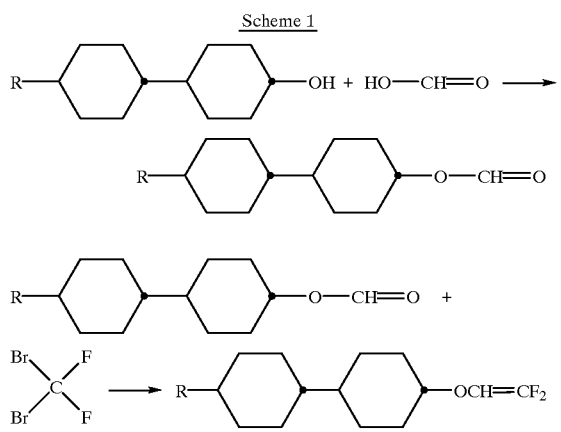

Scheme 1

The dielectrics may also contain further additives known to the person skilled in the art and described in the literature. For example, 0–15% of pleochroic dyes or chiral dopants can be added.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German Application No. 196 50 634.4, filed Dec. 6, 1996 is hereby incorporated by reference.

EXAMPLES

C denotes a crystalline phase, S a smectic phase, $S_B$ a smectic B phase, N a nematic phase and I the isotropic phase.

$V_o$ denotes the capacitive threshold voltage in a planar untwisted cell. $\Delta n$ denotes the optical anisotropoy and $n_o$ the ordinary refractive index (in each case at 589 nm). $\Delta \varepsilon$ denotes the dielectric anisotropy ($\Delta \varepsilon = \varepsilon_\| - \varepsilon_\perp$, where $\varepsilon_\|$ denotes the dielectric constant parallel to the longitudinal axes of the molecules and $\varepsilon_\perp$ denotes the dielectric constant perpendicular thereto). The electro-optical data were measured in a planar, untwisted cell at 20° C., unless expressly stated otherwise. The optical data were measured at 20° C., unless expressly stated otherwise.

In the present application and in the examples below, the structures of the liquid-crystal compounds are indicated by acronyms, the transformation into chemical formulae taking place as in Tables A and B below. All the radicals $C_nH_{2n+1}$- and $C_mH_{2m+1}$- are straight-chain alkyl radicals containing n respectively m carbon atoms. The coding in Table B is self-evident. In Table A, only the acronym for the parent structure is given. In individual cases, the acronym for the parent structure is followed, separated by a hyphen, by a code for the substituents $R^1$, $R^2$, $L^1$ and $L^2$.

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | F | H |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | F | H |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_2H_{2s}$— | CN | H | H |
| nAm | $C_nH_{2n+1}$ | $COOC_mH_{2m+1}$ | H | H |
| nF.F.F | $C_nH_{2n+1}$ | F | F | F |
| nCl.F.F | $C_nH_{2n+1}$ | Cl | F | F |
| nCF$_3$.F.F | $C_nH_{2n+1}$ | CF$_3$ | F | F |
| nOCF$_3$.F.F | $C_nH_{2n+1}$ | OCF$_3$ | F | F |
| nOCF$_2$.F.F | $C_nH_{2n+1}$ | OCHF$_2$ | F | F |
| nOCF$_3$.F | $C_nH_{2n+1}$ | OCF$_3$ | F | H |
| nCN.F.F | $C_nH_{2n+1}$ | CN | F | F |
| nCN.F | $C_nH_{2n+1}$ | CN | F | H |

TABLE A

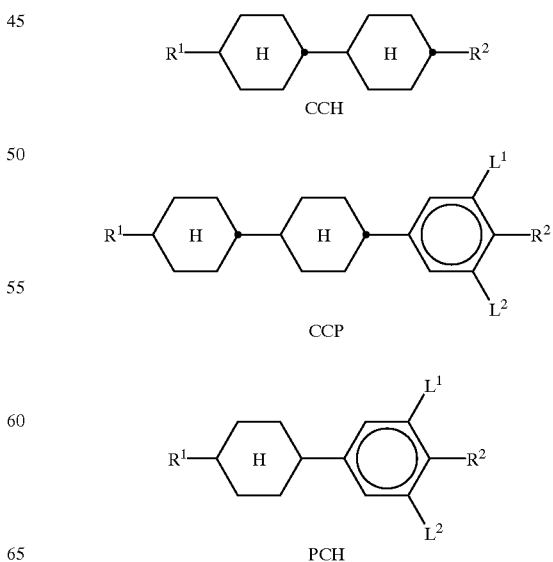

TABLE B

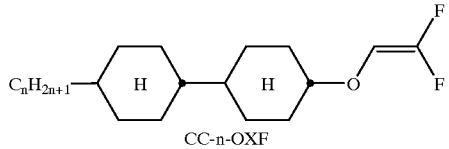

CC-n-OXF

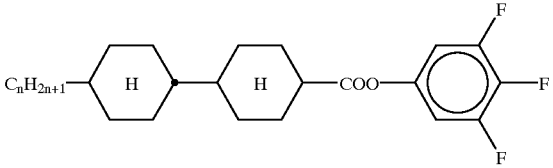

CCZU-n-F

Example 1

An IPS display contains a nematic mixture comprising

| | |
|---|---|
| CCP-2F.F.F | 9.00 |
| CCP-3F.F.F | 9.00 |
| CCP-5F.F.F | 6.00 |
| CCP-2OCF3 | 7.00 |
| CCP-3OCF$_3$ | 7.00 |
| CCP-4OCF$_3$ | 4.00 |
| PCH-2N.F.F | 5.00 |
| PCH-3N.F.F | 5.00 |
| PCH-5N.F.F | 5.00 |
| CCH-34 | 7.00 |
| CCH-35 | 7.00 |
| CCZU-2-F | 6.00 |
| CCZU-3-F | 12.00 |
| CCZU-5-F | 6.00 |
| CC-3-OXF | 3.00 |
| CC-5-OXF | 2.00 | and has the following properties:

| | |
|---|---|
| Clearing point | 70° C. |
| Δn | 0.0706 |
| Rotational viscosity | 87 mPa · s |
| V$_0$ | 0.87 V |

Comparative Example

An IPS display contains a nematic mixture comprising

| | |
|---|---|
| CCP-2F.F.F | 9.00 |
| CCP-3F.F.F | 9.00 |
| CCP-5F.F.F | 6.00 |
| CCP-2OCF3 | 6.00 |
| CCP-3OCF3 | 7.00 |
| CCP-4OCF3 | 4.00 |
| CCP-5OCF3 | 6.00 |
| PCH-2N.F.F | 5.00 |
| PCH-3N.F.F | 5.00 |
| PCH-5N.F.F | 5.00 |
| CCH-34 | 7.00 |
| CCH-35 | 7.00 |
| CCZU-2-F | 6.00 |

| | |
|---|---|
| CCZU-3-F | 12.00 |
| CCZU-5-F | 6.00 | and has the following properties:

| | |
|---|---|
| Clearing point | 77° C. |
| Δn | 0.0737 |
| Rotational viscosity | 99 mPa · s |
| V$_0$ | 0.99 V |

The threshold voltage is significantly higher than in the display from Example 1. The rotational viscosity of the mixture is also higher than that of Example 1, which results in a significantly longer response time.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An electro-optical liquid-crystal display having a realignment layer for realigning the liquid crystals whose field has a significant component parallel to the liquid-crystal layer and containing a liquid-crystalline medium of positive dielectric anisotropy which comprises at least one mesogenic compound of the formula II:

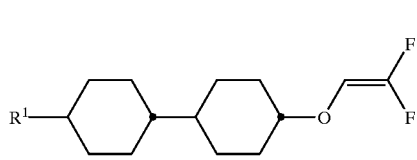

II in which

R' is an alkyl or alkenyl radical having 1 to 15 carbon atoms which is unsubstituted or monosubstituted to perhalo-substituted by halogen and in which one or more CH$_2$ groups are each, independently of one another, optionally replaced by —O—, —S—, —CO—, —COO—, —OCO— or —OCO—O— in such a way that O atoms are not linked directly to one another; and at least one compound selected from the formulae Ia, Ib and Ic:

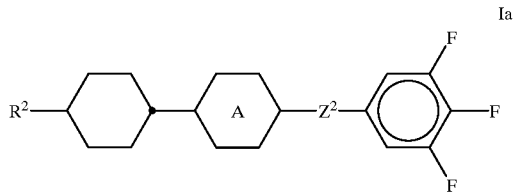

Ia

-continued

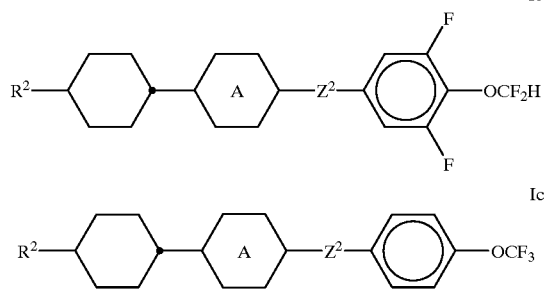

in which

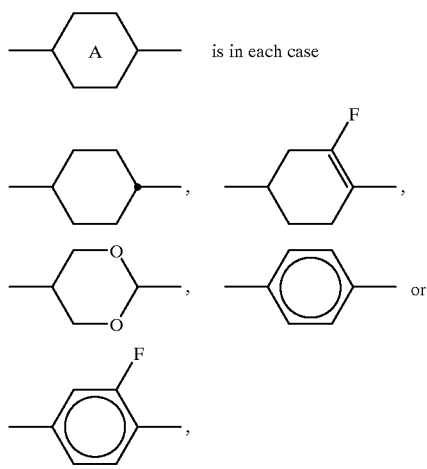

$Z^2$ is —COO—, —CH$_2$CH$_2$— or a single bond, and
$R^2$ is H, an alkyl or alkenyl radical having 1 to 15 carbon atoms which is unsubstituted, monosubstituted by CN or CF$_3$ or monosubstituted to perhalo-substituted by halogen, where one or more CH$_2$ groups in these radicals are optionally, in each case independently of one another, replaced by —O—, —S—,

—CO—, —CO—O—, —O—CO— or —O—CO—O— in such a way that O atoms are not linked directly to one another.

2. A liquid-crystal display according to claim 1, wherein the medium additionally comprises at least one compound of the formula I:

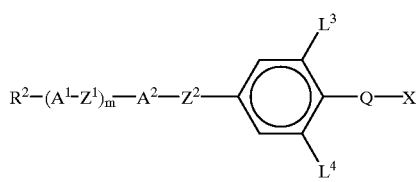

in which
$R^2$ is H, an alkyl or alkenyl radical having 1 to 15 carbon atoms which is unsubstituted, monosubstituted by CN or CF$_3$ or monosubstituted to perhalo-substituted by halogen, where one or more CH$_2$ groups in these radicals are optionally, in each case independently of one another, replaced by —O—, —S—,

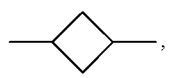

—CO—, —CO—O—, —O—CO— or —O—CO—O— in such a way that O atoms are not linked directly to one another,
Q is a radical of the formula:
—(O)$_q$—(CH$_2$)$_r$—(CF$_2$)$_s$— in which
q is 0 or 1,
r is 0 or an integer from 1 to 6, and
s is 0 or an integer from 1 to 6,
X is F or Cl, and in the case where s=1–6, is alternatively H, and
$A^1$ and $A^2$ are each, independently of one another,
(a) a trans-1,4-cyclohexylene radical or 1,4-cyclohexenylene radical, in which one or more non-adjacent CH$_2$ groups are optionally replaced by —O— and/or —S—,
(b) a 1,4-phenylene radical, in which one or two CH groups are optionally replaced by N, or
(c) a radical selected from the group consisting of 1,4-dicyclo[2.2.2]octylene, piperidine-1,4-diyl, naphthalene-2,6-diyl, decahydronaphthalene-2,6-diyl, and 1,2,3,4-tetrahydronaphthalene-2,6-diyl,
where the radicals (a) and (b) are optionally substituted by one or two fluorine atoms,
$L^3$ and $L^4$ are H or F,
$Z^1$ and $Z^2$ are each, independently of one another, —CO—O—, —O—CO—, —CH$_2$O—, —OCH$_2$—, —CH$_2$CH$_2$—, —CH=CH—, —C≡C—, or a single bond, or one of the radicals $Z^1$ and $Z^2$ is —(CH$_2$)$_4$— or —CH=CH—CH$_2$CH$_2$—, and
m is 0, 1 or 2.

3. A liquid-crystal display according to claim 1, wherein in the mesogenic compound of formula II, $R^1$ is an alkyl group having 1 to 8 carbon atoms.

4. A liquid-crystal display according to claim 2, wherein in the mesogenic compound of formula II, $R^1$ is an alkyl group having 1 to 8 carbon atoms.

5. A liquid-crystal display according to claim 1, wherein the liquid-crystalline medium contains at least one compound selected from the compounds of the formulae Ia, Ib, and Ic, wherein $Z^2$ is —COO—.

6. A liquid-crystal display according to claim 2, wherein the liquid-crystalline medium contains at least one compound selected from the compounds of the formulae Ia, Ib, and Ic, wherein $Z^2$ is —COO—.

7. A liquid-crystal display according to claim 1, wherein the liquid-crystalline medium contains at least one compound of formulae Ia, Ib, and Ic, wherein:

8. A liquid-crystal display according to claim 2, wherein the liquid-crystalline medium contains at least one compound of formulae Ia, Ib, and Ic, wherein:

9. A liquid crystal display according to claim 1, wherein the liquid-crystalline medium contains at least one compound of the formula Ia, wherein $Z^2$ is —COO—.

10. A liquid crystal display according to claim 2, wherein the liquid-crystalline medium contains at least one compound of the formula Ia, wherein $Z^2$ is —COO—.

11. A liquid-crystal display according to claim 1, wherein the liquid-crystalline medium additionally comprises at least one compound of the formula III:

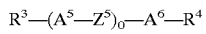   III in which
$R^3$ and $R^4$ are each, independently of one another, as defined for $R^2$ in formulae Ia, Ib and Ic,
$A^5$ and $A^6$ are each, independently of one another,
(a) a trans-1,4-cyclohexylene radical or 1,4-cyclohexenylene radical, in which one or more non-adjacent $CH_2$ groups are optionally replaced by —O— and/or —S—,
(b) a 1,4-phenylene radical, in which one or two CH groups are optionally replaced by N, or
(c) a radical selected from the group consisting of 1,4-dicyclo[2.2.2]octylene, piperidine-1,4-diyl, naphthalene-2,6-diyl, decahydronaphthalene-2,6-diyl, and 1,2,3,4-tetrahydronaphthalene-2,6-diyl, where the radicals (a) and (b) are optionally substituted by one or two fluorine atoms,
$Z^5$ is in each case, independently of the others, as defined for $Z^1$ and $Z^2$ in the formulae Ia, Ib and Ic, and
o is 1, 2 or 3.

12. A liquid-crystal display according to claim 2, wherein the liquid-crystalline medium additionally comprises at least one compound of the formula III:

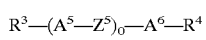   III in which
$R^3$ and $R^4$ are each, independently of one another, as defined for $R^2$ in formulae Ia, Ib and Ic,
$A^5$ and $A^6$ are each, independently of one another,
(a) a trans-1,4-cyclohexylene radical or 1,4-cyclohexenylene radical, in which one or more non-adjacent $CH_2$ groups are optionally replaced by —O— and/or —S—,
(b) a 1,4-phenylene radical, in which one or two CH groups are optionally replaced by N, or
(c) a radical selected from the group consisting of 1,4-dicyclo[2.2.2]octylene, piperidine-1,4-diyl, naphthalene-2,6-diyl, decahydronaphthalene-2,6-diyl, and 1,2,3,4-tetrahydronaphthalene-2,6-diyl, where the radicals (a) and (b) are optionally substituted by one or two fluorine atoms,
$Z^5$ is in each case, independently of the others, as defined for $Z^1$ and $Z^2$ in the formulae Ia, Ib and Ic, and
o is 1,2 or 3.

13. A liquid-crystal display according to claim 1, wherein the liquid-crystalline medium additionally comprises at least one compound of the formula IV:

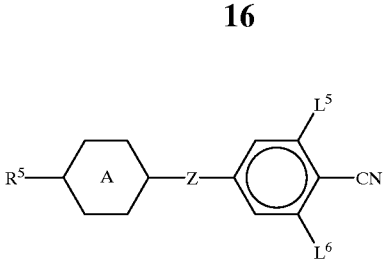

in which
$R^5$ is as defined for $R^2$ in formula Ia, Ib and Ic,

is a single bond or —COO—, and
$L^5$ and $L^6$ are each F or H.

14. A liquid-crystal display according to claim 2, wherein the liquid-crystalline medium additionally comprises at least one compound of the formula IV:

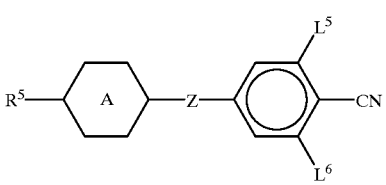

in which
$R^5$ is as defined for $R^2$ in formula Ia, Ib and Ic,

Z is a single bond or —COO—, and
$L^5$ and $L^6$ are each F or H.

15. A display according to claim 1, having pixels addressed by means of an active matrix.

16. A liquid-crystalline medium of positive dielectric anisotropy which comprises at least one mesogenic compound of formula II:

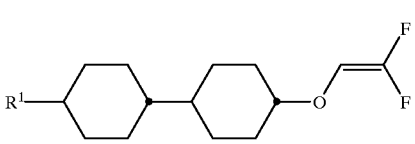

in which
$R^1$ is an alkyl of alkenyl radical having 1 to 15 carbon atoms which is unsubstituted or monosubstituted to perhalo-substituted by halogen and in which one or more $CH_2$ groups are each, independently of one another, optionally replaced by —O—, —S—, —CO—, —COO—, —OCO— or —OCO—O— in such a way that O atoms are not linked directly to one another, and
at least one compound selected of the formulae Ia, Ib and Ic:

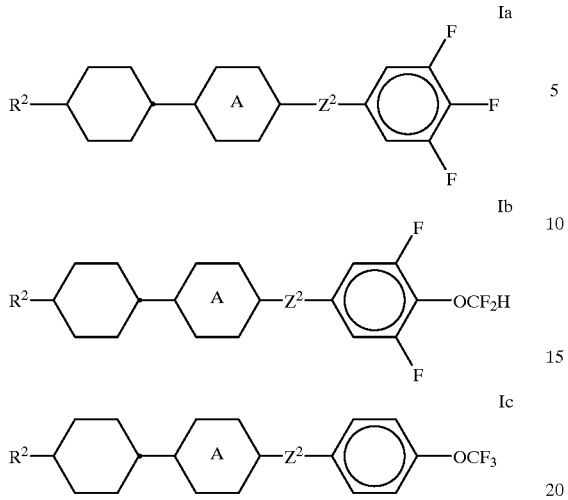

in which

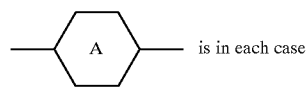
is in each case

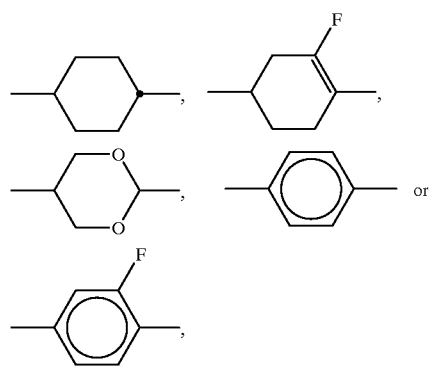

$Z^2$ is —COO—, —CH$_2$CH$_2$— or a single bond, and
$R^2$ is H, an alkyl or alkenyl radical having 1 to 15 carbon atoms which is unsubstituted, monosubstituted by CN or CF$_3$ or monosubstituted to perhalo-substituted by halogen, where one or more CH$_2$ groups in these radicals are optionally, in each case independently of one another, replaced by —O—, —S—,

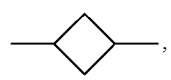

—CO—, —CO—O—, —O—CO— or —O—CO—O— in such a way that O atoms are not linked directly to one another.

17. A liquid-crystalline medium according to claim 16, which comprises:

from 50 to 95% by weight of at least one compound of the formulae Ia, Ib or Ic, from 2 to 25% by weight of at least one compound of the formula II, from 0 to 30% by weight of at least one compound of the formula III,

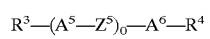

in which
$R^3$ and $R^4$ are each, independently of one another, as defined for $R^2$ in the formulae Ia, Ib and Ic,
$A^5$ and $A^6$ are each, independently of one another,
  (a) a trans-1,4-cyclohexylene radical or 1,4-cyclohexenylene radical, in which one or more non-adjacent CH$_2$ groups are optionally replaced by —O— and/or —S—,
  (b) a 1,4-phenylene radical, in which one or two CH groups are optionally replaced by N, or
  (c) a radical selected from the group consisting of 1,4-dicyclo[2.2.2]octylene, piperidine-1,4-diyl, naphthalene-2,6-diyl, decahydronaphthalene-2,6-diyl, and 1,2,3,4-tetrahydronaphthalene-2,6-diyl, where the radicals (a) and (b) are optionally substituted by one or two fluorine atoms,
$Z^5$ is in each case, independently of the others, as defined for $Z^1$ and $Z^2$ in the formulae Ia, Ib and Ic, and
o is 1, 2 or 3, and from 5 to 35% by weight of a compound of the formula IV:

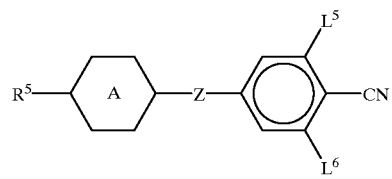

in which
$R^5$ is as defined for $R^2$ in formulae Ia, Ib and Ic,

Z is a single bond or —COO—, and
$L^5$ and $L^6$ are each F or H.

18. A liquid-crystalline medium of claim 17, which comprises:

from 60 to 80% by weight of at least one compound of the formulae Ia, Ib or Ic, from 3 to 15% by weight of at least one compound of the formula II, from 5 to 25% by weight of at least one compound of the formula III, and from 8 to 25% by weight of at least one compound of the formula IV.

* * * * *